US008333767B2

(12) United States Patent
Dorf

(10) Patent No.: US 8,333,767 B2
(45) Date of Patent: Dec. 18, 2012

(54) CERCLAGE DEVICE

(76) Inventor: Erik Dorf, Breckenridge, CO (US)

( * ) Notice: Subject to any disclaimer, the term of this patent is extended or adjusted under 35 U.S.C. 154(b) by 180 days.

(21) Appl. No.: 12/769,402

(22) Filed: Apr. 28, 2010

(65) Prior Publication Data

US 2011/0270253 A1 Nov. 3, 2011

(51) Int. Cl.
*A61B 17/56* (2006.01)
*A61B 17/58* (2006.01)
*A61B 17/82* (2006.01)
*A61F 2/30* (2006.01)

(52) U.S. Cl. ......... 606/74; 606/103; 606/144; 606/148
(58) Field of Classification Search ........... 606/144, 606/148, 145–147, 149, 150, 99, 86 A, 86 B, 606/74, 53–105.5, 263
See application file for complete search history.

(56) References Cited

U.S. PATENT DOCUMENTS

| | | | | |
|---|---|---|---|---|
| 5,447,512 A | * | 9/1995 | Wilson et al. ............. | 606/139 |
| 5,562,685 A | * | 10/1996 | Mollenauer et al. .......... | 606/144 |
| 5,573,542 A | * | 11/1996 | Stevens .................. | 606/144 |
| 5,607,440 A | * | 3/1997 | Danks et al. ............. | 606/185 |
| 5,720,754 A | * | 2/1998 | Middleman et al. ......... | 606/127 |
| 5,810,832 A | | 9/1998 | Blasingame et al. | |
| 5,851,209 A | | 12/1998 | Kummer et al. | |
| 6,527,785 B2 | * | 3/2003 | Sancoff et al. ............. | 606/148 |
| 2004/0010264 A1 | | 1/2004 | Acker et al. | |
| 2004/0176802 A1 | * | 9/2004 | Skiba et al. ............. | 606/222 |
| 2006/0264977 A1 | * | 11/2006 | Dana et al. ............. | 606/148 |
| 2009/0082788 A1 | * | 3/2009 | ElMaraghy ............. | 606/148 |

\* cited by examiner

*Primary Examiner* — Thomas Barrett
*Assistant Examiner* — Si M Lee
(74) *Attorney, Agent, or Firm* — Larson & Anderson, LLC

(57) ABSTRACT

A cerclage device includes a base member, a cerclage member, and a drive member. The base member has a length sufficient to allow for manual holding by a user, an interior space extending from a distal end toward a proximal end, and a slot extending from the distal end toward the proximal end. The cerclage member has a long side with a proximal end and a distal end and a curvature in one direction about its long side at least at the distal end. The cerclage member allows for attaching a suture and fits within and is straightened by the base member within the interior space when in a retracted position. When the drive member is attached to the cerclage member movement of the engagement portion in the slot pushes and pulls the cerclage member to/from the straightened position from/to the extended curved position.

20 Claims, 5 Drawing Sheets

CERCLAGE DEVICE

BACKGROUND

When individuals (human or any other living being) suffer a bone break, orthopaedic surgeons (or some other skilled person such as a veterinarian or physicians assistant) are often called upon to reduce the fractured bone. When surgery is necessary to reduce the fracture the surgeon may secure broken and/or fragmented pieces of bone by encircling the broken and/or fragmented bone with a suture material (e.g. a wire or a cable). In this cerclage procedure, a suture, cable, or wire is passed around the bone, drawn tightly, and secured. Bone cerclage procedures are well known in the art.

Surgical instruments useful for passing a suture material around a bone are also known. However, it has become increasingly important for physicians to perform familiar surgical techniques in a minimally invasive manner. Minimally invasive surgery results in less surgical trauma to the patient. These surgeries require smaller incisions, smaller and more precise instrumentation, less operating time, and result in less soft tissue trauma with similar or better patient outcomes. The value of minimally invasive surgical techniques is vast, because less soft tissue damage may result in speedier recoveries, less time off of work and less dependence on pain medication. Any minimally invasive surgical technique, however, requires not only a skilled surgeon, but also specially designed surgical tools. Therefore, a need for such surgical instruments is ever present.

SUMMARY OF INVENTION

The present invention provides a minimally invasive cerclage device for use in the operating room or in the field on a human or any other living being. In accordance with one embodiment of the present invention, a cerclage device includes a base member, a cerclage member, and a drive member.

The base member of the device has: a length sufficient to allow for manual holding by a user and preferably a length sufficient to allow for passage through soft tissue; an interior space extending from a distal end toward a proximal end; and a slot extending from the distal end toward the proximal end of the base member and connecting the interior space to the exterior of the base member.

The cerclage member of the device has a long side with a proximal end and a distal end and a curvature in one direction about its long side at least at the distal end. The cerclage member has means (e.g. a protrusion, a depression, and/or a detachable tip) for attaching a suture toward its distal end (e.g. at its distal end). The cerclage member fits within and is straightened by the base member within its interior space when the device is in a retracted position. When the device is in an extended curved position the distal end of the cerclage member is extended out of the interior space of the base member at its distal end.

The drive member of the device is attached or attachable to the cerclage member of the device. The drive member has an engagement portion that is disposed at least partially through the slot of the base member and is slidable within the slot. When the drive member is attached to the cerclage member, movement of the engagement portion in the slot pushes and pulls the cerclage member of the device between the retracted straightened position and the extended curved position.

DETAILED DESCRIPTION

Reference throughout the specification to "one embodiment," "another embodiment," "an embodiment," "some embodiments," and so forth, means that a particular element (e.g., feature, structure, property, and/or characteristic) described in connection with the embodiment is included in at least one embodiment described herein, and may or may not be present in other embodiments. In addition, it is to be understood that the described element(s) may be combined in any suitable manner in the various embodiments.

Cerclage instruments useful for passing a suture around bone are known in the art. For Example cerclage devices are described in U.S. Pat. Nos. 5,573,542, 5,810,832, and 5,851,209, and also in US Patent Application Publication No. 2004/0010264, all of which are incorporated herein by reference.

These devices, while attempting to minimize the invasive nature of surgery, still require large incisions multiple instruments including wound spreaders to complete the surgery. Therefore, surgeries using these devices are not necessarily considered to be minimally invasive. Furthermore, these devices are large canulated end-drive cerclage devices. The present Inventor has found that using these type of cerclage devices provides little to no tactile sensation with regard to movement of the cerclage member around the bone during operation of the device. With little tactile sensation a surgeon using these end-drive devices can inadvertently sever blood vessels, arteries, nerves, and connective tissue during the cerclage procedure. Furthermore, since these prior art devices are canulated, reuse of the devices requires additional and sometimes difficult and expensive cleaning/sterilization processes.

Figure 1A:
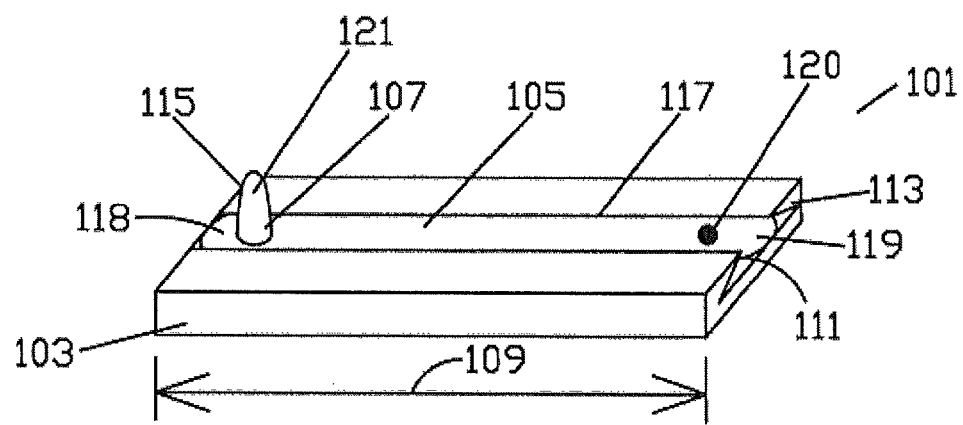
FIGS. 1A and 1B are isometric views of a cerclage device in accordance with the present invention.
Figure 1B:
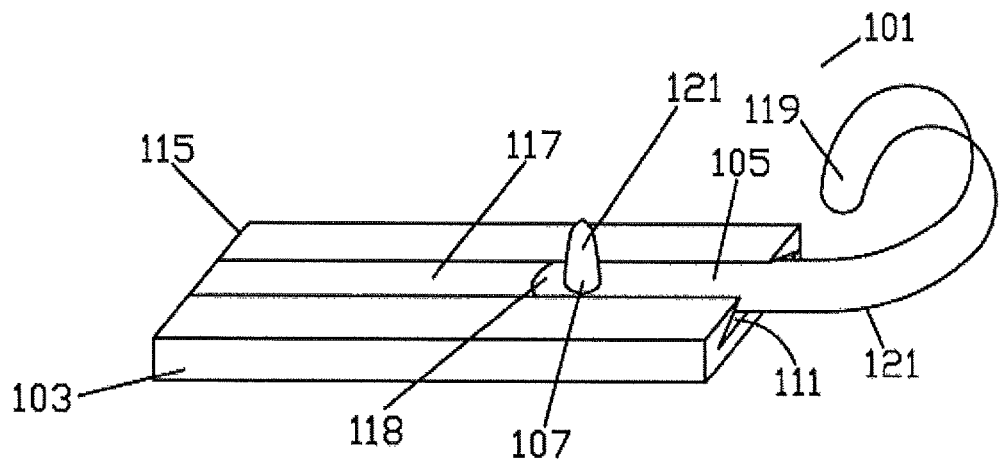

The present cerclage device overcomes these, and other, deficiencies. In a first embodiment a cerclage device is provided. FIG. 1A, shows the cerclage device 101 in a retracted flattened position and FIG. 1B shows the cerclage device in an extended curved position. The cerclage device 101 has a base member 103, a cerclage member 105, and a drive member 107.

The base member 103 has a length 109 sufficient to allow for manual holding of the base member by a user (e.g. surgeon or a physicians assistant) and preferably a length sufficient to allow passage through the soft tissue of a patient in a specified procedure. The base member 103 has an interior space 111 extending from a distal end 113 towards a proximal end 115. The base also has a slot 117 extending from the distal end 113 toward the proximal end 115 and connecting the interior space 111 to the exterior (e.g. outside) of the base.

In a preferred embodiment the base member will contain ergonomic features on its outer surface. The features may include palm and/or finger grooves to enable comfortable and non-slip holding of the device by a user. The material of construction of the base member is not particularly limited. However, in one embodiment the base member may be made of a thermosetting polymer where a user can customize the base member to the contours of their hand. As described below, it is preferably that the material of construction however be rigid so as to allow the transfer of tactile sensation, or vibration, along the base member to a user as the device is being used. Where the base member is sterilizable and reusable it may be preferred that the base member is formed from a more expensive material such as metal (e.g. stainless steel) or lighter weight material (e.g. carbon fiber).

In another preferred embodiment, the base member will be narrower and/or thinner toward its distal end. In this embodiment, the narrower and/or thinner portion is sufficient to allow for passage of the base member through soft tissue of a patient to allow the distal end of the device/base member to come near or into contact with a fractured bone to be reduced. In this embodiment, the narrower and/or thinner portion is more easily passed between and/or through soft tissue during operation of the device. In this embodiment, the base member may be thicker and/or contain the ergonomic features described above toward its proximal end to allow for more comfortable and precise operation of the device. In one embodiment, depending on the specific bone to be repaired and/or the nature and depth of the cerclage procedure within a patient, the narrower and/or thinner portion of the base member may make up between 1/10th and 3/4 (e.g. between 1/10th to 1/2) of the length of the base member, or between 1/8th and 1/3rd the length of the base member (e.g. between 1/4 inch and 20 inches, between 1/2 inch and 10 inches, between 1 inch and 6 inches, or between 2 and 5 inches).

The cerclage member 105 has a long side 121 ending at a proximal end 118 and a distal end 119. The cerclage member 105 has an curvature in one direction about its long side 121 at least at the distal end 119. The cerclage member 105 fits within and is straightened by the base member within the interior space 111 when in a retracted position (shown in FIG. 1A). When in an extended curved position (shown in FIG. 1B) the distal end 119 of the member 105 is extended out of the interior space 111 at the distal end 113 of the base member 103. The cerclage member 105 also has means for attaching a suture 120.

The cerclage member preferably has an intrinsic curvature and is formed from a material that has a preset radius of curvature that approximates the radius of curvature of the bone for which it is being used to pass a cerclage suture wire around. For example where an adult femur fracture is to be reduced by a surgeon, a typical radius of curvature of the cerclage member will be between 1/2 inch and 1 inch. Radii of curvature variations for other surgeries can be envisioned and do not depart from the scope of the present invention.

The base member deforms the cerclage member when it straightens it within its internal space in the retracted position and returns it to its "natural" curved state when in the extended position outside of the internal space of the base member. In other words, the cerclage member has a "shape memory" that biases the cerclage member into its curved state. Preferably the cerclage device is kept in its extended curved shape and sold and transported in its extended curved shape or even disassembled shape to maintain the "shape memory" of the cerclage member in its curved state.

In another embodiment, the base member may be reuseable while the cerclage member is disposable. In this embodiment, the disposable cerclage member may be sold and distributed in various packages have specific radii of curvature to be selected by a surgeon for a given bone reduction surgery. The cerclage member would preferably be distributed in a curved state, with or without an attached suture for use with a sterilized and reusable base member.

In the preferred embodiment shown in FIGS. 1A and 1B the cerclage member 105 comprises a sheet having a generally rectangular cross section with a distal end 119 and a curvature in one direction about its long side 121 at least at the distal end 119. The sheet of the cerclage member 105 fits within and is flattened by the interior space 111 when in a retracted flattened position (as shown in FIG. 1A). In this embodiment the sheet has a top major surface and a bottom major surface wherein top major surface and the bottom major surface are preferably taper toward each other, at least toward their distal ends, to form a leading edge at the distal end the cerclage member.

Figure 3A:
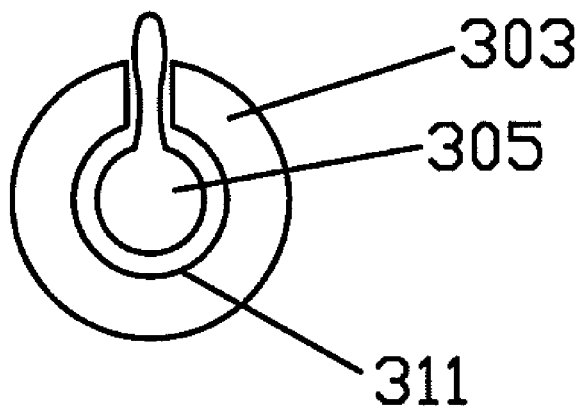
Figure 3B:
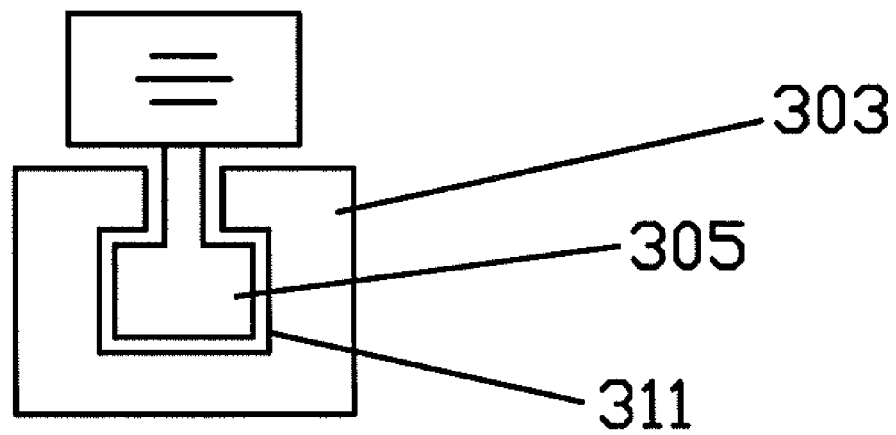

The cerclage member, the base member, and the internal space may have different shapes. As shown in FIG. 3A the cerclage member 305, the base member 303, and the interior space 311 are mostly cylindrical (e.g. the cross-section of the interior space and/or the cerclage member is circular, oval, or ovoid). As shown in FIG. 3B the cerclage member 305, the base member 303, and the interior space 311 have sides and are cubical (e.g. the cross-section of the interior space and/or the cerclage member is square, or rectangular) or triangular.

The cerclage member also include means for attaching a suture (e.g. metal wire, polymer, synthetic fiber, natural fiber, or dissolvable fiber) to the cerclage member. These means are not particularly limited. Preferably the suture material (e.g. metal wire) will be attached toward the distal end of the cerclage member (e.g. at the very end or close thereto), so that only passage of the distal end of the cerclage member is required to encircle the fractured bone with the suture. Once the suture is visible on the other side of the bone the surgeon may remove it from the cerclage member and retract the cerclage member and device from the wound. However, it is also contemplated that the attachment means will provide for the suture material to be attached to the proximal end of the cerclage member, so that the entire cerclage member will be passed around the bone and removed from the wound to pass the suture around the bone.

The means for attaching a suture may be a protrusion or depression formed on the distal end of the member to interact and attach the suture. The means may also be an aperture formed through the cerclage member, wherein the suture passes through aperture to attach it to the member.

Figure 4:
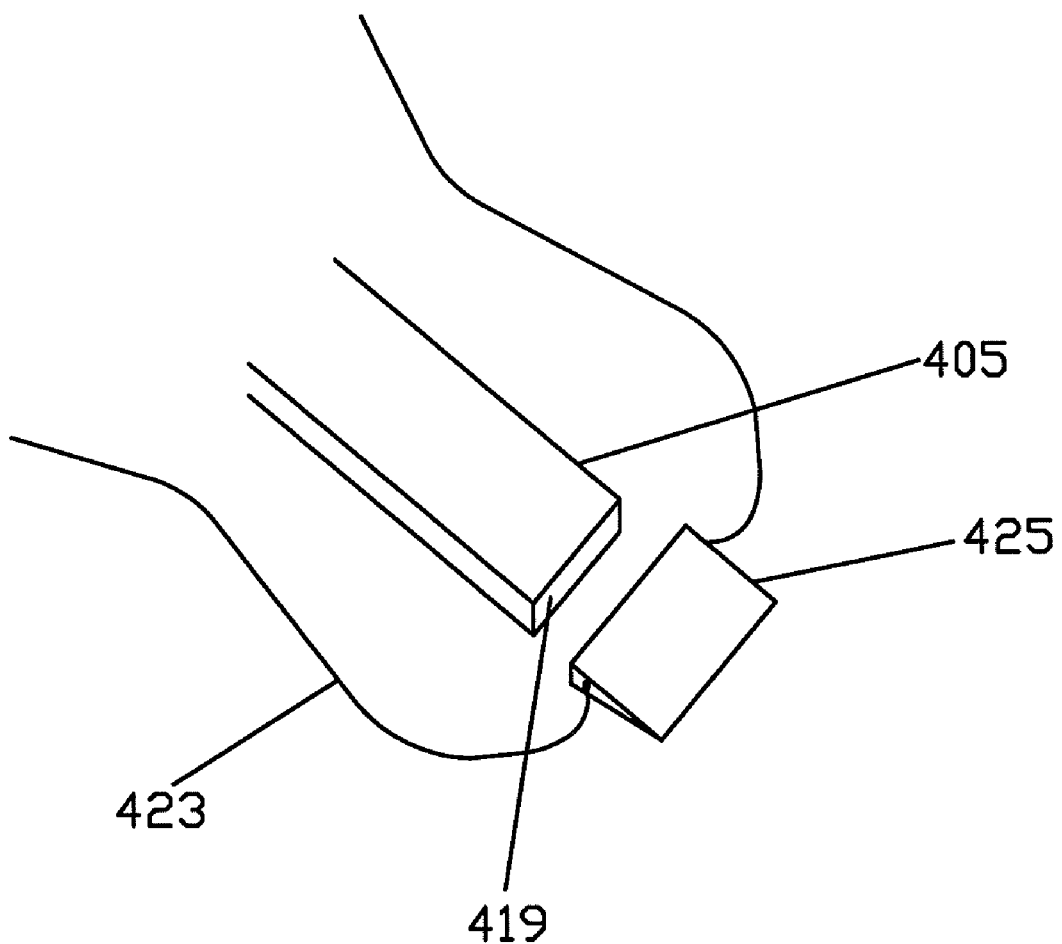
FIG. 4 is an isometric view of a cerclage member and an attachable suture tip.

In another embodiment, shown in FIG. 4, the means for attaching the suture 423 to cerclage member 405 includes an attachable tip 425 for attaching to the distal end 419 of the cerclage member 405. The attachable tip 425 holds a suture 423 (e.g. for example in a protrusion, depression, or aperture as such is describe above) and when attached to the cerclage member 405 attaches the suture 423 to the cerclage member. The attachable tip will preferably have a receiving depression for receiving the distal end 419 of the cerclage member 405. The distal end 419 of the cerclage member 405 may have barbs, or some other feature, for preventing the tip 425 from being removed with ordinary force (i.e. force that does not destroy the device) from the cerclage member 405 after it has been attached. In another embodiment the tip 425 is removable from the cerclage member 405 using ordinary force (e.g by pulling on the tip). In the later embodiment where the tip is removable it is preferred that ordinary force is required to remove the tip 425 and that it simply can't fall off by shaking or by the inversion (e.g gravity).

Referring again to FIGS. 1A and 1B, the drive member 107 is attached or attachable to the cerclage member 105. The drive member 107 has an engagement portion 121 that is disposed at least partially through, more preferably entirely through, the slot 111. The drive member 107 is slidable within the slot of the base member 103.

The engagement portion 221 of the drive member 207 is likewise not particularly limited other than it extends at least partially through slot 217 of the base member 203. The engagement portion 221 may be physically and/or manually engaged by the hand or fingertips of a user. In another embodiment the engagement portion 221 may be retrofitted and/or engaged by the hand or fingertips of a user through a separate handle or attachment attached to the engagement portion or directly to the drive member. In this later embodiment the retrofit handle/attachment may be specifically selected by a user depending on personal choice or preference.

Figure 2A:
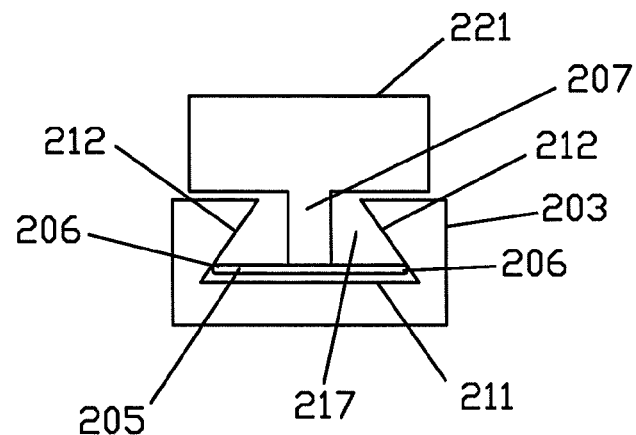
FIGS. 2A, 2B, 2C, 3A, 3B, and 5 are end views of cerclage devices in accordance with the present invention.
Figure 2B:
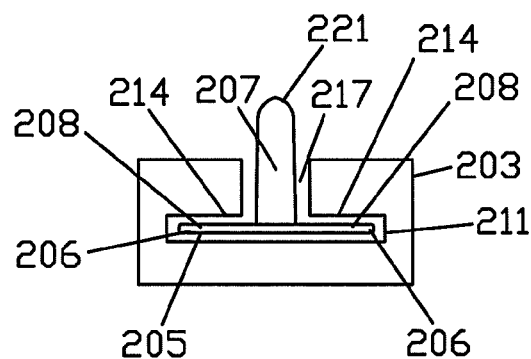
Figure 2C:
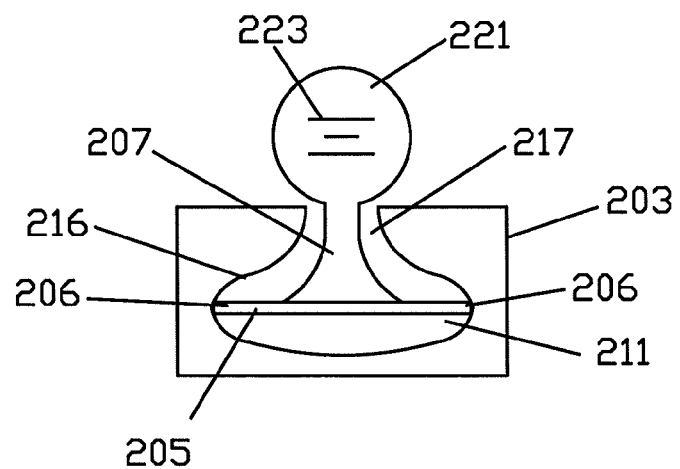

In preferred embodiments, the engagement portion 221 is made of a thin material that allows transmission of tactile sensation (e.g. vibration) from the cerclage member through the engagement portion 217 to the user (e.g. surgeon). FIGS. 2A through 2C show various configuration of the engagement portion 221 of the drive member 207. In FIG. 2A the engagement portion 221 of drive member 207 is formed as square or rectangular pushing and pulling knob that rides along the exterior surface of the base member 203. In FIG. 2B the engagement portion 221 of drive member 207 is a long protrusion extending through the slot to the exterior of the base member 203. In FIG. 2C the engagement portion 221 of drive member 207 is formed as circular or oval pushing and pulling knob that extends through the slot to the exterior of the base member 203. In FIG. 2C the circular knob also includes demonstrates raised gripping ridges 223 that can be included on any of the possible engagement portions. In another embodiment, not depicted, the engagement portion may be detachable from and re-attachable to the drive member using normal force. In this embodiment, the user may selected a preferred or customized engagement portion for use with the device.

During operation of the cerclage device 101, when the drive member 107 is attached to the cerclage member 105, movement of the drive member 107 in the slot 117 in first direction pushes the cerclage member from the straightened position, shown in FIG. 1A, to the extended curved position, shown in FIG. 1B. Movement of the drive member 107 in the slot 117 in a second direction opposite the first direction pulls the cerclage member from the extended curved position to the straightened position.

As discussed above, the shape of the base member 103 and interior space 111 are not particular limited other than upon retraction of the cerclage member 105, the interior space 111 is sized and shaped to straighten the cerclage member 105. In a preferred embodiment, as shown in FIGS. 2A-2C, the cerclage member 205 will have a rectangular cross-section shape. The thickness (e.g. height of the cross section) of the cerclage member is preferably in a range of between 0.1 to 2.0 mm (e.g. about 1.0 mm). In this embodiment, the shape of the interior space 211 is not particularly limited other than it is sufficient to flatten the cerclage member 205.

The cerclage member and drive member are preferably made of materials selected and sized to allow for the transmission of vibration from the distal end of the cerclage member along its length to and through the engagement portion of the drive member. For example the cerclage member may be made of a thin spring metal sheet (e.g. spring steel) and the drive member and the base member made of metal or rigid injection molded polymer. Again the cerclage member will have a predetermined natural radius of curvature selected for a specific operation. Too long of a radius of curvature will result in a wayward cerclage member tip inadvertently passing through and damaging soft tissue rather than hugging the surface of a bone at a predetermined depth.

FIGS. 2A through 2C show shapes of the interior space 211 that are sufficient to flatten the cerclage member 205 (here a member having a thin rectangular cross section) when it is received in the interior space 211 of the base member 203. FIG. 2A shows the interior space 211 being formed in a trapezoidal shape wherein the interaction of the edges 206 of cerclage sheet 205 with the angled walls 212 of the interior space 211 serve to flatten cerclage sheet 205 when it is retracted. FIG. 2B shows the interior space 211 being formed in a rectangular shape wherein the interaction of the edges 206 of the cerclage sheet 205 and the flat portion 208 of cerclage sheet 205 with the top walls 214 of the interior space 211 serve to flatten cerclage sheet 205 when it is retracted. FIG. 2C shows the interior space 211 being formed in an oval shape wherein the interaction of the edges 206 of the cerclage sheet 205 with the oval wall 216 of the interior space 211 serve to flatten cerclage sheet 205 when it is retracted. Where the base member is intended to be reused in multiple procedures, it is sometimes preferred that the interior space have the rounded wall feature similar to that as shown in FIG. 2C. It has been found that devices with rounded surface are more easily sterilized as compared to devices having corners or edges (e.g. the interior space 211 as shown in FIGS. 2A and 2B). Where the base member is to be cleaned and reused in later surgeries, it may be preferable to minimize sharp corners. In this case the interior space shape of FIG. 2C may be preferred.

Figure 5:
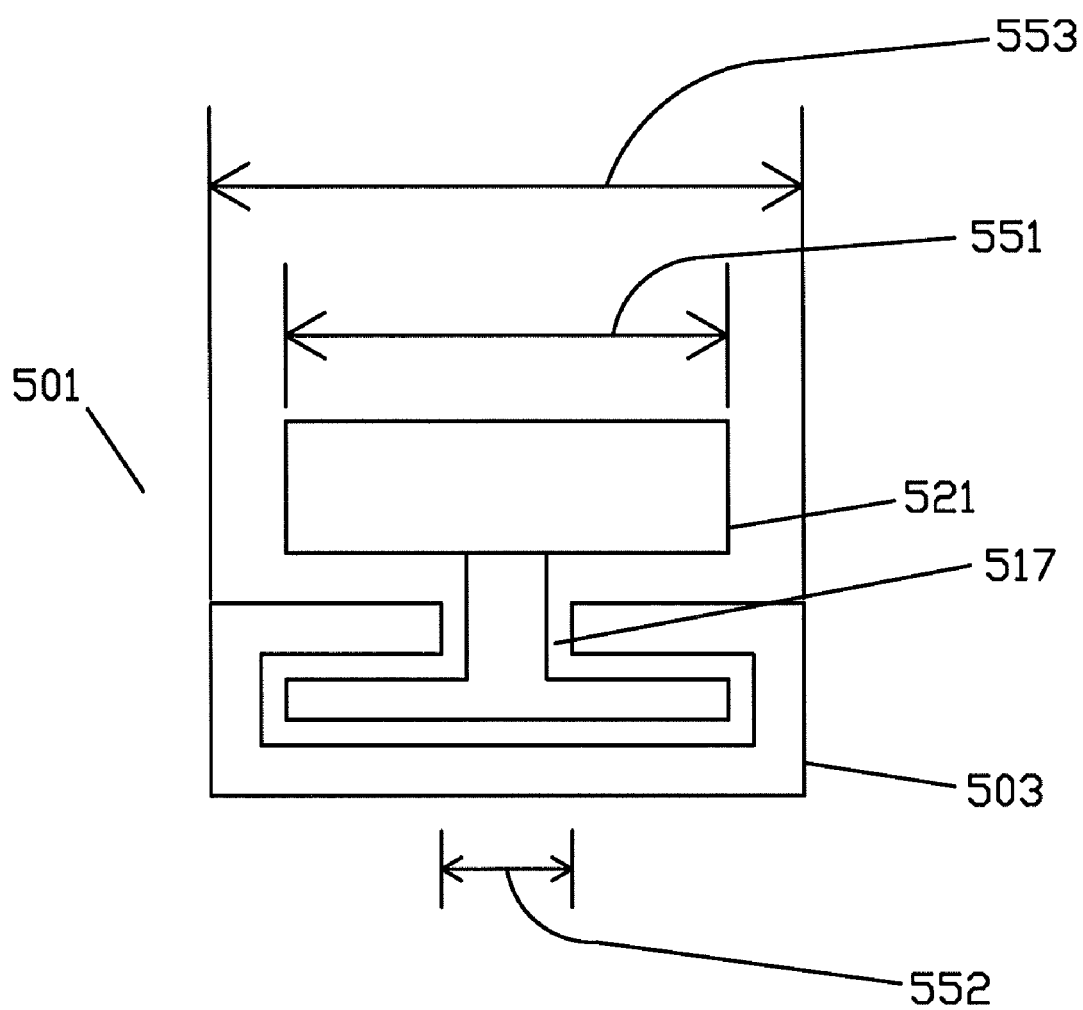

In the embodiment depicted in FIG. 5, the engagement portion 521 of the cerclage member has a width 551, the slot 517 has a width 552, and the base member 503 has a width 553. During operation of the device 501 the widths 551, 552, and 553, lie in parallel directions to one another. In this embodiment, the width 551 of the engagement portion 521 is greater than the width 552 of the slot 517 and smaller than the width 553 of the base member 503.

The invention claimed is:

1. A cerclage device comprising a base member, a cerclage member, and a drive member, wherein:
   (I) the base member has:
      a length sufficient to allow for manual holding by a user,
      an interior space extending from a distal end toward a proximal end, and
      a slot extending from the distal end toward the proximal end and connecting the interior space to the exterior,
   (II) the cerclage member is non-cannulated, has a long side with a proximal end and a distal end, and a curvature in one direction about its long side at least at the distal end, wherein the cerclage member fits within and is straightened by the base member within the interior space when in a retracted position, and wherein when in an extended curved position the distal end of the cerclage member is extended out of the interior space at the distal end of the base member,
   the cerclage member comprising means for attaching a suture, and
   (III) the drive member has an engagement portion, is attached or attachable to the cerclage member, and is disposed at least partially through the slot and is slidable within the slot,
   wherein during operation of the cerclage device when the drive member is attached to the cerclage member movement of the drive member in the slot in first direction pushes the cerclage member from a straightened position to the extended curved position and movement of the drive member in the slot in a second direction opposite the first direction pulls the cerclage member from the extended curved position to the straightened position.

2. The device of claim 1, wherein the means for attaching a suture includes a protrusion or depression formed on or in the cerclage member toward the distal end thereof, wherein the suture may interact with the protrusion or depression to attach the suture to the cerclage member.

3. The device of claim 1, wherein the means for attaching a suture includes an aperture formed through the cerclage member toward the distal end thereof, wherein the suture may pass through the aperture to attach the suture to the cerclage member.

4. The device of claim 1, wherein the means for attaching a suture comprises an attachable tip for attaching to the distal end of the cerclage member, the attachable tip holding a suture and thereby attaching the suture to the cerclage member when the attachable tip is attached to the cerclage member.

5. The device of claim 4, wherein the attachable tip includes a protrusion or depression formed on or in the cerclage member toward the distal end thereof, wherein the suture may interact with the protrusion or depression to attach the suture to the cerclage member when the attachable tip is attached to the cerclage member.

6. The device of claim 4, wherein the attachable tip includes an aperture formed through the cerclage member toward the distal end thereof, wherein the suture may pass through the aperture to attach the suture to the cerclage member when the attachable tip is attached to the cerclage member.

7. The device of claim 4, wherein the attachable tip is also detachable from the distal end of the cerclage member after it has been attached.

8. The device of claim 7, wherein the slot has a width, the base member has a width, and the engagement portion has a width, wherein during operation of the device the widths lie in parallel directions to one another and wherein the width of the engagement portion is greater than the width of the slot and smaller than the width of the base member.

9. The device of claim 1, wherein the cerclage member and drive member are made of materials selected and sized to allow for the transmission of vibration from the distal end of the cerclage member along its length to and through the engagement portion of the drive member.

10. The device of claim 9, wherein the cerclage member is made of a thin spring metal sheet.

11. The device of claim 10, wherein the drive member and the base member made of metal, rigid injection molded polymer, or carbon fiber.

12. The device of claim 1, wherein the cerclage member further comprises a wire suture material attached thereto.

13. The device of claim 1, wherein the cerclage member has a cross-section shape selected from the group consisting of round, oval, ovoid, square, rectangular, and triangular.

14. The device of claim 13, wherein the interior space has a cross-section shape matching the cross-section shape of the cerclage member.

15. The device of claim 1, wherein the cerclage member is a sheet having a generally rectangular cross section with a distal end and a radius of curvature in one direction about its long side at least at the distal end,
wherein the cerclage member fits within and is flattened by the base member within the interior space when in a retracted flattened position, and wherein when in an extended curved position the distal end of the cerclage member is extended out of the interior space at the distal end of the base member,
the cerclage member comprising means for attaching a suture, and
the drive member is attached or attachable to the cerclage member and has an engagement portion that disposed at least partially through the slot and is slidable within the slot, wherein
during operation of the cerclage device, when the drive member is attached to the cerclage member, movement of the engagement portion in the slot in first direction pushes the cerclage member from the flattened position to the extended curved position and movement of the engagement portion in the slot in a second direction opposite the first direction pulls the cerclage member from the extended curved position to the flattened position.

16. The device of claim 15, wherein the cerclage member has a top major surface and a bottom major surface, wherein top major surface and the bottom major surface taper toward each other to form a leading edge at the distal end the cerclage member.

17. The device of claim 1, wherein the base member also has a length sufficient to allow for passage through soft tissue.

18. The device of claim 17, wherein the length sufficient to allow for passage through soft tissue is between 1/10th and 1/2 of the length of the base member.

19. The device of claim 1, wherein the cerclage member has a radius of curvature dependent upon the radius a human bone selected for a cerclage procedure.

20. A cerclage device comprising a base member, a cerclage member, and a drive member, wherein:
(I) the base member has:
a length sufficient to allow for manual holding by a user and a length sufficient to allow for passage 1/10th and 1/2 of the length of the base member,
an interior space having a rectangular cross section and a length extending from a distal end toward a proximal end, and
a slot extending from the distal end toward the proximal end and connecting the interior space to the exterior,
(II) the cerclage member is a non-cannulated flat sheet of spring metal having a rectangular cross section and a length with a proximate and distal end and a curvature in one direction about its long side at least at the distal end,
wherein the cerclage member fits within and is flattened by the base member within the interior space when in a retracted flattened position, and wherein when in an extended curved position the distal end of the sheet is extended out of the interior space at the distal end of the base member,
the cerclage member comprising means for attaching a wire suture and a wire suture attached thereto,
(III) the drive member is attached or attachable to the cerclage member and has an engagement portion that disposed at least partially through the slot and is slidable within the slot, wherein
during operation of the cerclage device, when the drive member is attached to the cerclage member, movement of the engagement portion in the slot in first direction pushes the cerclage member from the flattened position to the extended curved position and movement of the engagement portion in the slot in a second direction opposite the first direction pulls the cerclage member from the extended curved position to the flattened position.

* * * * *